United States Patent [19]
Cole et al.

[11] Patent Number: 6,100,028
[45] Date of Patent: Aug. 8, 2000

[54] DNA POLYMERASE EXTENSION ASSAY

[75] Inventors: James L. Cole, Doylestown; Lawrence C. Kuo, Solebury; David B. Olsen, Lansdale, all of Pa.

[73] Assignee: Merck & Co., Inc., Rahway, N.J.

[21] Appl. No.: 08/973,139

[22] PCT Filed: Jun. 3, 1996

[86] PCT No.: PCT/US96/08330

§ 371 Date: Jul. 31, 1998

§ 102(e) Date: Jul. 31, 1998

[87] PCT Pub. No.: WO96/40994

PCT Pub. Date: Dec. 19, 1996

[51] Int. Cl.[7] .............................. C12Q 1/68; C12P 19/34
[52] U.S. Cl. ............................................. 435/6; 435/91.31
[58] Field of Search ........................... 435/6, 91.1, 91.31, 435/91.32, 91.5, 91.51, 91.53, 195, 196, 199; 536/23.1, 24.3, 24.33, 25.3, 25.32

[56] References Cited

U.S. PATENT DOCUMENTS

| | | | |
|---|---|---|---|
| 4,521,509 | 6/1985 | Benkovic | 435/6 |
| 5,660,989 | 8/1997 | Cole et al. | 435/6 |

FOREIGN PATENT DOCUMENTS

| | | |
|---|---|---|
| 0 300 796 | 1/1989 | European Pat. Off. . |
| WO 96/40993 | 12/1996 | WIPO . |

OTHER PUBLICATIONS

Chung, et al., "Biochemical studies on capped RNA primers identify a class of oligonucleotide . . . ", Proceedings of the National Academy of Sciences of the USA, vol. 91, No. 6, pp. 2372–2376, Mar. 15, 1994.

Clark, et al., "Novel non–templated nucleotide addition reactions catalyzed by proaryotic and eucaryotic CNA polymers", Lab. of Mole., vol. 16, No. 20, pp. 9677–9687, 1988.

Plotch, et al., "A Unique Cap (m GpppXm)–Dependent Influenza Virion Endonuclease Cleaves Capped RNAs . . . " A Uni. Cap. Cell., vol. 23, pp. 847–858, 1981.

Plotch, et al., "Influenza Virion Transcriptase: Synthesis In Vitro of Large, Polyadenylic Acid–Containing . . . ", Infl. Vir. Trans. J. of Virol., vol. 21, No. 1, pp. 24–34 (1977).

Tabor, et al., "Selective Inactivation of the Exonuclease Activity of Bacteriophage T7 DNA Polymerase . . . ", Sel. Inact. J. of Bio. Chem., vol. 264, No. 11, pp. 6447–6458 (1989).

Selnick, et al., "Inhibition of Cap (m7GpppXm)–Dependent Enconuclease of Influenza Virus by 4–Substituted . . . ",Antimicrob. Agents and Chemo., vol. 38, No. 12, pp. 2827–2837, 1994.

Pyle, et al., "Ribozymes: A Distinct Class of Metalloenzymes", Science, vol. 261, pp. 709–714, Aug. 6, 1993.

Shi, et al., "Influenza A Zirus RNA Polymerase Subunit PB2 Is the Endonuclease which Cleaves Host Cell mRNA . . . ", Virology, vol. 208, pp. 38–47, 1995.

Fedor, et al., "Substrate sequence effects on "hammerhead" RNA catalytic efficiency", Proc. Natl. Acad. Sci., vol. 87, pp. 1668–1672, Mar. 1990.

Kuppuswamy, et al., "Single nucleotide primer extension to detect genetic diseases: Experimental application . . . ", Proc. Natl. Acad. Sci., vol. 88, pp. 1143–1147, Feb. 1991.

AMERSHAM Life Sciences Catalogue, 1993.

*Primary Examiner*—David Guzo
*Assistant Examiner*—Thomas G. Larson
*Attorney, Agent, or Firm*—Michael D. Yablonsky; Jack L. Tribble

[57] ABSTRACT

The present invention provides rapid accurate sensitive assays specific for the detection of at least one a single stranded oligonucleotide produced by the action of an enzyme on a substrate. The assays are useful to detect the presence in a sample of an enzyme which acts on an oligonucleotide substrate to generate a single stranded oligonucleotide product and to detect inhibitors of such an enzyme.

6 Claims, 4 Drawing Sheets

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear    (iii) HYPOTHETICAL: NO    (iv) ANTI-SENSE: NO    (xi) SEQUENCE DESCRIPTION: SEQ ID NO:1:

GUUUUUAUUU UUAAUUUUC                              19

(2) INFORMATION FOR SEQ ID NO:2:

(i) SEQUENCE CHARACTERISTICS:
      (A) LENGTH: 13 base pairs
      (B) TYPE: nucleic acid
      (C) STRANDEDNESS: single
      (D) TOPOLOGY: linear    (iii) HYPOTHETICAL: NO    (iv) ANTI-SENSE: NO

```
        (xi) SEQUENCE DESCRIPTION: SEQ ID NO:2:

ACACUUGCUU UUG                                                          13

(2) INFORMATION FOR SEQ ID NO:3:

(i) SEQUENCE CHARACTERISTICS:
          (A) LENGTH: 13 base pairs
          (B) TYPE: nucleic acid
          (C) STRANDEDNESS: single
          (D) TOPOLOGY: linear (iii) HYPOTHETICAL: NO (iv) ANTI-SENSE: NO (xi) SEQUENCE DESCRIPTION: SEQ ID NO:3:

GTTTTTATTT TTA                                                          13

(2) INFORMATION FOR SEQ ID NO:4:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (iii) HYPOTHETICAL: NO (iv) ANTI-SENSE: NO (xi) SEQUENCE DESCRIPTION: SEQ ID NO:4:

CCCCCCCCCC TAAAAATAAA AAC                                               23

(2) INFORMATION FOR SEQ ID NO:5:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (iii) HYPOTHETICAL: NO (iv) ANTI-SENSE: NO (xi) SEQUENCE DESCRIPTION: SEQ ID NO:5:

CCCCCCCCCC TTAAAAATAA AAAC                                              24
```

DNA POLYMERASE EXTENSION ASSAY

This is a national stage filing of PCT application US96/08330, filed Jun. 3, 1996, and a continuation of U.S. Ser. No. 08/487,760, filed Jun. 07, 1995, now abandoned.

FIELD OF THE INVENTION

This invention relates to a novel sensitive assay to detect and quantify the presence of an enzyme which acts to produce a single-stranded oligonucleotide product, or to inhibitors of such enzyme.

BACKGROUND OF THE INVENTION

Enzymes which use polynucleotides as substrates are often fundamental to the biochemical function of many organisms and viruses. This group of enzymes includes, for example, endonucleases, exonucleases and ribozymes. A number of enzymes act on substrates to give single-stranded oligonucleotide products. For example, the influenza virus endonuclease cleaves capped host cell transcripts 10 to 13 bases from the 5' end. Sequence specific RNA endonucleases are known; for example the 2–5A-dependent RNase found in higher animals functions to cleave single-stranded regions of RNA 3' of UpNp dimers, with a preference for UU and UA sequences. In addition, ribozymes are known to cleave single-stranded RNAs at specific recognition sequences.

While it is recognized that inhibitors or activators of these enzymes might be new classes of therapeutic or preventative compounds, particularly against viral diseases, identification of such compounds has been hampered by the lack of a convenient assay system.

An ideal enzyme assay system should have: a) high throughput; b) the ability to distinguish enzyme-catalyzed cleavage from nonspecific nucleotide cleavage; and c) high sensitivity. Previous nucleotide cleavage assays involved the use of polyacrylamide gel electrophoresis to separate product from substrate (Plotch et al., 1981 Cell 23:847–858) which is not convenient for processing large numbers of samples.

DETAILED DESCRIPTION OF THE INVENTION

This invention is directed to a novel, accurate, sensitive, rapid assay which is specific for a chosen enzyme which acts on a substrate to produce a single-stranded oligonucleotide product. This invention comprises a method of detecting the enzyme activity of a sample suspected of containing either an enzyme which acts on an oligonucleotide substrate to generate a single-stranded oligonucleotide product, or an inhibitor of such enzyme comprising:

a) adding an oligonucleotide substrate to the sample whose activity is to be assayed to generate a single-stranded oligonucleotide product;

b) hybridizing the single-stranded oligonucleotide product with a DNA template, said DNA template comprising a first segment substantially complementary to the oligonucleotide product and a template 5'-extension region attached to the first segment, said extension region comprising at least one nucleotide, under hybridization conditions to form a RNA: DNA heteroduplex or a DNA:DNA duplex;

c) adding labeled mononucleotide which is complementary to the second segment of the DNA template;

d) adding a DNA polymerase to the heteroduplex or duplex under conditions permitting the DNA polymerase to catalyze the addition of the labeled mononucleotide to the 3'-end of the oligonucleotide product to produce a labeled polymerase product; and e) measuring the amount of labeled polymerase product as a measure of the amount of enzyme activity of the sample.

A further embodiment of this invention is a method of determining the site where an endonuclease cleaves an oligonucleotide substrate to create a cleavage product comprising:

a) preparing at least one DNA template sample, wherein the DNA comprises a first 3'-segment putatively complementary to the cleavage product and of the same length as the cleavage product, and further comprising a 5'-extension region comprising at least one nucleotide;

b) adding cleavage product to the sample under hybridizing conditions to form a RNA:DNA heteroduplex or DNA:DNA duplex;

c) adding to the sample labeled mononucleotide which is complementary to the 5'-extension region;

d) adding to the sample DNA polymerase under conditions permitting a polymerase reaction to occur wherein the labeled nucleotide is added to the 3'-end of the cleavage product if the 3'-segment of the DNA template is complementary to the cleavage product and of the same length as the cleavage product; and e) determining if the reaction of step d) occurs.

In accordance with this invention, the sample to be analyzed may contain an unknown quantity of an enzyme which acts on an oligonucleotide substrate (either DNA or RNA) to produce a single-stranded oligonucleotide product. Examples of such enzymes include various endonucleases, including either DNA or RNA endonucleases and ribozymes. Especially preferred are viral endonucleases and ribozymes.

In one embodiment of the invention, the amount of enzyme present in a sample may be quantified. In an alternative embodiment, the sample may contain a known amount of enzyme, and a substance whose inhibitory activity is to be determined. The amount of labeled polymerase product is compared to the amount of labeled polymerase product produced by a control sample where no inhibitors were present, and the degree of inhibitory activity present in the sample can be determined.

In another aspect of this invention, the assay can be used to easily identify the position where the enzyme cleaves its substrate. In this embodiment of the assay, at least one, and preferably a series of DNA templates is made, each having a different length, and each having a 5'-extension region. Endonuclease cleavage product is added. If the DNA template complementarity region is complementary to the cleavage product and the same length as the cleavage product, it will hybridize and a polymerase addition reaction can occur. If the template complementarity region is not the same length as the cleavage product so that the 3'-OH of the cleavage product cannot prime polymerization, the polymerase reaction will not occur.

In another embodiment of this invention, ribozyme activity, rather than endonuclease activity is determined using this assay.

To determine the amount of labeled polymerase product present, any detection method may be employed. A preferred method is to pass the sample containing labeled polymerase product and excess labeled mononucleotide through a filter which traps the labeled polymerase product and determining the amount of labeled polymerase product which has been trapped on the filter.

DEFINITIONS

Throughout the specification and claims the following definitions shall apply:

"nt" is the abbreviation for nucleotide.

"AlMV" is the abbreviation for Alfalfa Mosaid Virus.

"Substantially complementary" means that there is sufficient complementarity so that under the experimental conditions employed, the 3' region of the primer will hybridize with the DNA template strand such that the duplex so formed is capable of serving as a substrate for a DNA polymerase. "Substantially complementary" further requires that there is sufficient complementarity so that a duplex can form and that the duplex has sufficient stability so that its melting temperature is greater than the freezing point of the solvent system. In cases where the substrate is RNA, then "substantially complementary" means that there is sufficient complementarity so that the 3'-region of the RNA primer will hybridize with the DNA template strand such that the heteroduplex is capable of serving as a substrate for a DNA polymerase; further there is sufficient complementarity so that the heteroduplex will form and it has sufficient stability so that its melting temperature is greater than the freezing point of the solvent system.

"Oligonucleotide" is at least two nucleotides in length.

"Substantially repeated" means that the oligonucleotide is made up of at least 80% of the same base, preferably at least 90% of the same base, and even more preferably at least 95% of the same base.

"Derived from AlMV" means that the oligonucleotide is at least 80% homologous to the 5'-end of the AlMV 4 RNA, and is able to act as a substrate of influenza endonuclease, i.e. it can be cleaved by influenza endonuclease.

"Ribozyme" is a type of enzyme which is made of RNA rather than protein.

"Enzyme" is meant to include various biological molecules having catalytic functions, regardless of whether the molecule is proteinaceous, and specifically includes ribozymes.

The substrate can be any oligonucleotide substrate, either DNA or RNA, which is acted upon by an enzyme to produce a single-stranded oligonucleotide product. It may be modified, i.e., by a 5'-cap, if the enzyme requires this type of substrate. Capped oligonucleotide products may be made according to the procedure set forth in U.S. Pat. No. 5,861,501, granted Jan. 19, 1999, on U.S. Ser. No. 08/807,104, filed Feb. 04, 1997 as a divisional of U.S. Ser. No. 08/480,068, filed Jun. 07, 1995, filed herewith, which is hereby incorporated by reference. In one embodiment, the assay uses 5'-capped RNA which is cleaved by the influenza endonuclease. A 5'-capped RNA precursor may made according to the procedure set forth in the above referenced U.S. Pat. No. 5,861,501 to make a 19 nt RNA containing a 5'-triphosphate. This is then treated with a guanylyltransferase, as described in U.S. Pat. No. 5,660,989, granted Aug. 26, 1997 on U.S. Ser. No. 08/487,759, filed Jun. 07, 1995, which is hereby incorporated by reference. Guanylyl transferases are well known and may be obtained commercially; for example, Vaccinia virus guanylyltransferase may be purchased from Bethesda Research Laboratories, Gaithersburg, Md. The result is a 19 nt 5'-capped RNA substrate which is cleaved by the influenza endonuclease, generating a 13 nt product. Preferably, the endonuclease substrate is derived from the 5' end of the AlMV 4 RNA, which has been previously demonstrated to be a substrate for the influenza endonuclease and is cleaved at nucleotide A13.

In an alternate preferred embodiment, the enzyme is a ribozyme, such as a hammerhead ribozyme, hairpin ribozyme or a Group I intron type ribozyme and the substrate is an RNA molecule. As ribozymes generally require the presence of a divalent ion to function, it is important that these be present in the assay reaction mixture. Depending on the particular ribozyme chosen, the known important ions which are needed for activity include: divalent metal cations such as $Zn^{+2}$, $Mn^{+2}$, $Mg^{+2}$, or $Ca^{+2}$. The oligonucleotide substrate is then cleaved by the ribozyme in the presence of the cation.

The oligonucleotide product is then used as a primer for a DNA polymerase-catalyzed extension reaction. In order for the polymerase extension reaction to proceed, a DNA template is required. The DNA template is a two-part molecule it contains a 3'-region which is substantially complementary to the oligonucleotide product, joined to a template 5'-extension region. Although in theory the 5'-extension region may be made from any desired nucleotides, it is preferred that they be substantially repeated nucleotides, and that the nucleotides present in the extension region are not present in the 3'-complementarity region in order to achieve specificity for product cleaved at the correct position. In the most preferred embodiment, the 5'-extension region is made up of repeated nucleotides. If the 5'-extension region is not made from substantially repeated nucleotides, then there may be specificity problems with the assay, unless the extension region is quite long to amplify the signal of the correct cleavage product relative to non-specific products.

There is no particular limit as to the length of the extension region; it may be as short as a single nucleotide or as long as existing synthesis methods permit (up to or exceeding 50 nucleotides). In preferred embodiments, the 5'-extension region is at least one nucleotide residue in length, and is more preferably at least about 10 residues in length. Thus, the template extension region should preferably be a poly-dC, a poly-dG, a poly-dA, or a poly-dT region. In one preferred embodiment of this invention, the template extension region is a poly-dC residue 10 nt in length.

Figure 1:
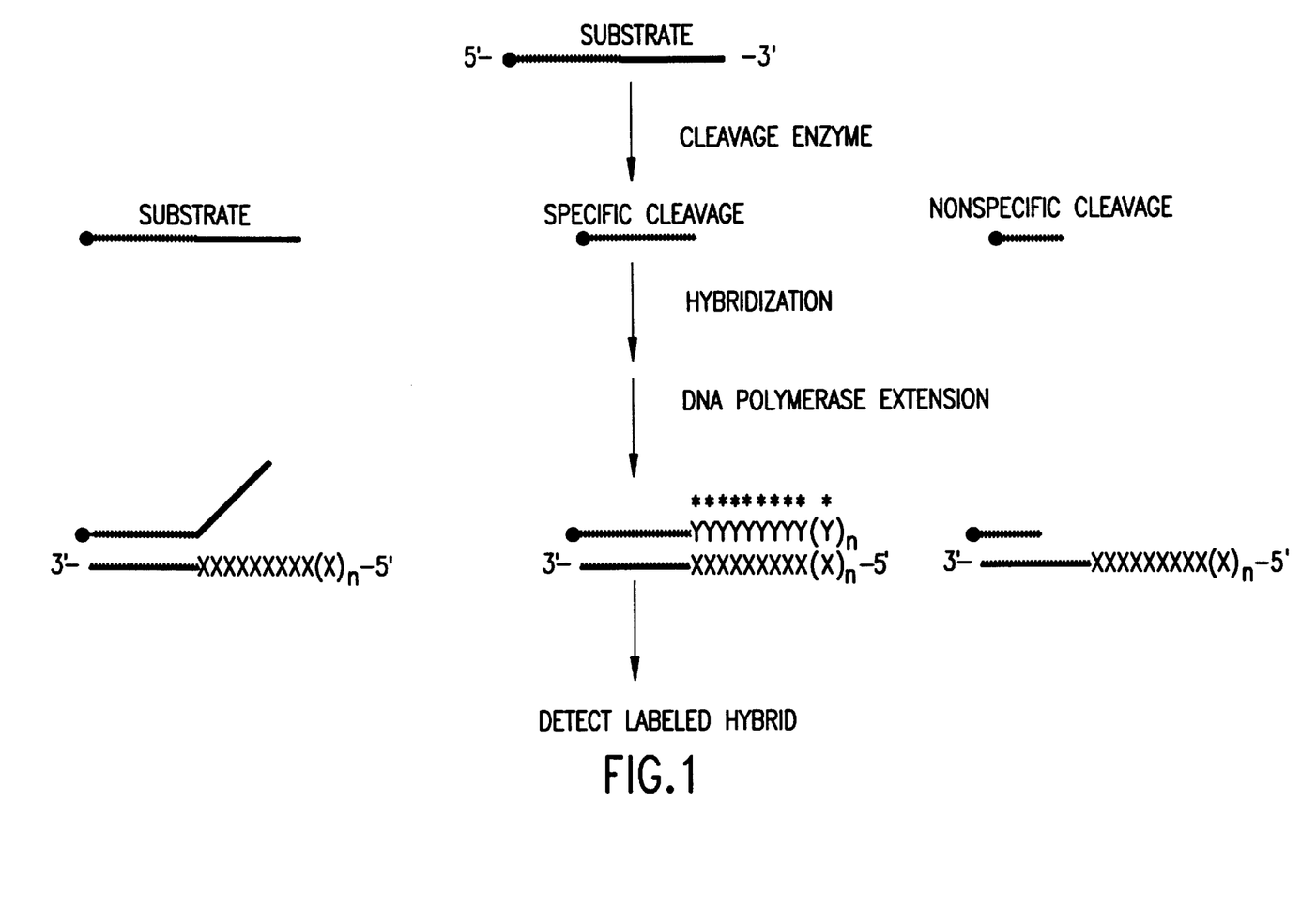
FIG. 1 is a flowchart illustrating the DNA polymerase extension assay of this invention.

During the DNA polymerase-catalyzed extension reaction, the oligonucleotide product will be extended in length by labeled nucleotides which are complementary to the nucleotides present in the DNA template extension region. For example, if the template extension region is a 10 residue poly-C, the oligonucleotide product will be extended 10 bases by a labeled poly-G sequence. While any type of label which is conventionally used in the nucleotide assay arts may be used to label the nucleotides which will be incorporated into the product extension region, such as fluorescent or absorption labels, it is preferred to use a radiolabel. In a preferred embodiment, the product extension region is poly-$\alpha$-$^{32}$P labeled dGMP (as shown in FIG. 1).

In addition, to prevent a polymerase-catalyzed extension from occurring on the 3'-OH end of the template, the 3'-OH of the primer is preferably blocked. Numerous blocking materials are known and suitable, and include cordycepin (3'-deoxyadenosine) and other 3'-moieties without a 3'-OH. In one embodiment of this invention, the 3'-OH is blocked with a (3-amino-2-hydroxy)propoxyphosphoryl. In another embodiment of this invention, the 3'-OH is blocked by introduction of a 3'-3'-A-5' linkage. While it is possible to run an assay of this invention without blocking the 3'-OH of the primer, blocking the 3'-OH end helps to prevent background signals and this helps to increase the sensitivity of the assay.

Numerous DNA polymerase enzymes are known and may be used in the DNA polymerase reaction step of this invention. In one embodiment, where the enzyme substrate is an RNA, Sequenase® Version 2, a mutant of bacteriophage T7 DNA polymerase (obtained from United States Biochemicals, Cleveland, Ohio) in which the 3' to 5' exonuclease activity is abolished by in vitro mutagenesis (Tabor et al., 1989 *J. Biol. Chem* 264:6447–6458) is a preferred DNA polymerase. This polymerase is preferred because it is able to use oligoribonucleotides as primers, it replicates with high fidelity and does not have a 3' to 5' "proofreading" activity.

Depending on the type of label used, detection of the labeled hybrid polymerase product may be achieved by any appropriate means. Generally this may include a step of separating labeled mononucleotide from labeled hybrid polymerase product. In a preferred embodiment, detection is achieved by filtering the sample mixture (which at this point in the assay method, contains the labeled hybrid polymerase product and excess labeled mono-nucleotide) through a nylon membrane. The unincorporated labeled mononucleotides flow through the membrane while the labeled hybrid polymerase reaction product is captured. If the label was a radiolabel, then the amount of radioactivity bound to the filter may be quantified using a phosphorimager or by a plate reading scintillation counter.

This assay has distinct advantages over the prior art assays in that it does not involve an electrophoresis step and may be run in 96-well microtiter plate format. Other key advantages of the assay of this invention are that it monitors the substrate cleavage reaction only at the correct position in the sequence, thereby discriminating against nonspecific cleavage products. Also importantly, this assay is sensitive enough to detect 200 attomoles ($2 \times 10^{-16}$ moles) of product generated in a typical cleavage reaction.

The specificity of the preferred embodiment assays of this invention is achieved through the choice of the DNA template and the high fidelity of the T7 DNA Sequenase® polymerase. Under the conditions of a typical reaction more than 90% of the substrate is not cleaved, but this does not interfere with the specificity of the assay because the uncleaved RNA substrate does not serve as a primer for polymerization since the 3' end cannot base-pair to the template. In addition, nonspecific cleavage products, such as those which have been cleaved at a site different than the enzyme cleavage site are not extended. Although these shorter (or longer) sequences may hybridize with the template, they are not extended by the DNA polymerase because this reaction would require the presence of nucleotides which are not present in the reaction mixture.

The polymerase extension reaction is dependent on hybridization of the primer onto the DNA template. Therefore, for effective hybridization of the primer to the DNA template, polymerase extension reactions are preferably carried out at least 10° C. below the melting temperature of the primer:template complex. A typical preferred reaction temperature is 0° C. for a primer:template complex with a melting temperature of 14° C.

Figure 2A:
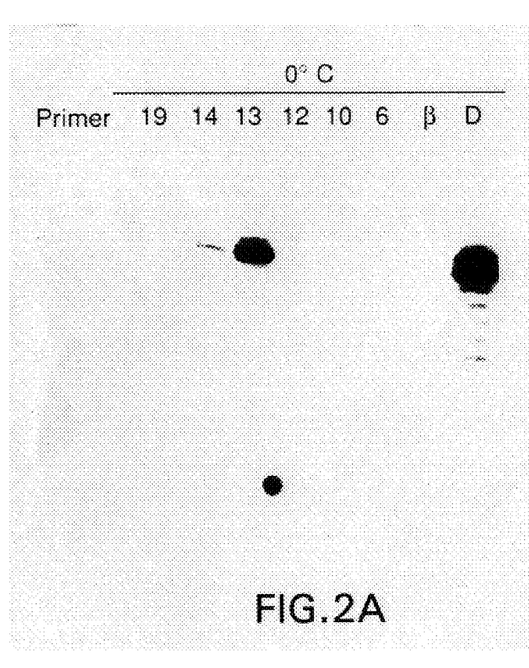
FIG. 2 (Parts A–B) is a photograph of a phosphorimager scan of a 20% acrylamide 8M urea polyacrylamide gel demonstrating the effects of primer length and temperature on polymerase-catalyzed extension reactions. The lane labeled 19 corresponds to an uncapped RNA primer (19 nt) with the sequence of the AlMV substrate (5'-GUUUUUAUUUUUAAUUUUC-3')(SEQ.ID.NO.:1); lanes labeled 14-6 correspond to RNA primers of the indicated length derived from 3' deletions of the 19 nt primer. The lane labeled β corresponds to a 13 nt RNA derived from the 5' end of β-globin mRNA (5'-ACACUUGCUUUUG-3') (SEQ.ID.NO.:2). The lane labeled D corresponds to a 13 nt DNA with the AlMV primer sequence (5'-GTTTTTATTTTTA-3') (SEQ.ID.NO.:3).
Figure 2B:
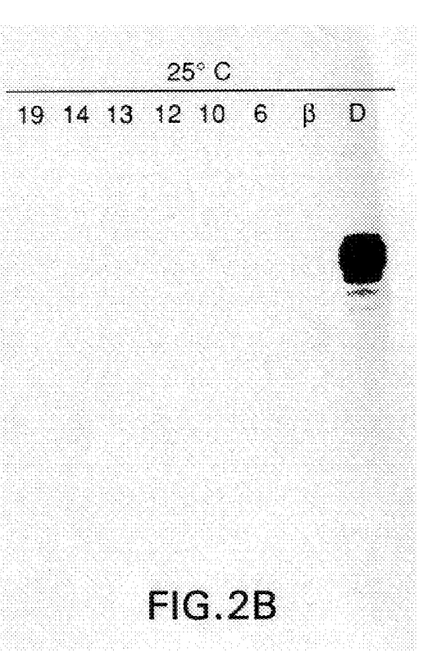

FIG. 2 illustrates the specificity of the polymerase-catalyzed extension reaction and the effects of temperature. In an influenza endonuclease assay, a capped AlMV RNA substrate which is cleaved into a 13 nt RNA product is used. Synthetic, uncapped RNA and DNA primers of various lengths and sequence were hybridized with the DNA template and extended with polymerase and $\alpha^{32}$P-dGTP. When the reaction is carried out at 0° C. the only primers that give efficient extension are the 13 nt AlMV RNA and the corresponding sequence in DNA. Although incompletely extended products are visible on the gel, the reaction conditions have been optimized such that the most intense band corresponds to complete primer extension. A fainter band above the most intense band corresponds to a single base addition. Several DNA polymerases are known to catalyze the addition of a single base onto the 3'-OH termini of a blunt-ended DNA (Clark, 1988 *Nucl. Acids Res.* 16:9677–9686); presumably, a similar activity is also present in the Sequenase® polymerase that was used. The much less intense bands in the lane containing 14 nt RNA primer are attributable to a small contaminant of the 13 nt RNA present in the 14 nt ribonucleotide. No extension products are observed using either the full length 19 nt primer, AlMV primers smaller than 13 nt, or a heterologous 13 nt RNA derived from the 5' end of the β-globin transcript (5'-ACACUUGCUUUUG-3') (SEQ.ID.NO.:2). The Polymerase® reaction selectively extends the AlMV 13 nt primers and discriminates against sequences corresponding to uncleaved AlMV substrate or shorter nonspecific cleavage products. It is noteworthy that the high fidelity of Sequenase® prevents incorrect extension of AlMV primers differing in length by as little as a single base.

Figure 3:
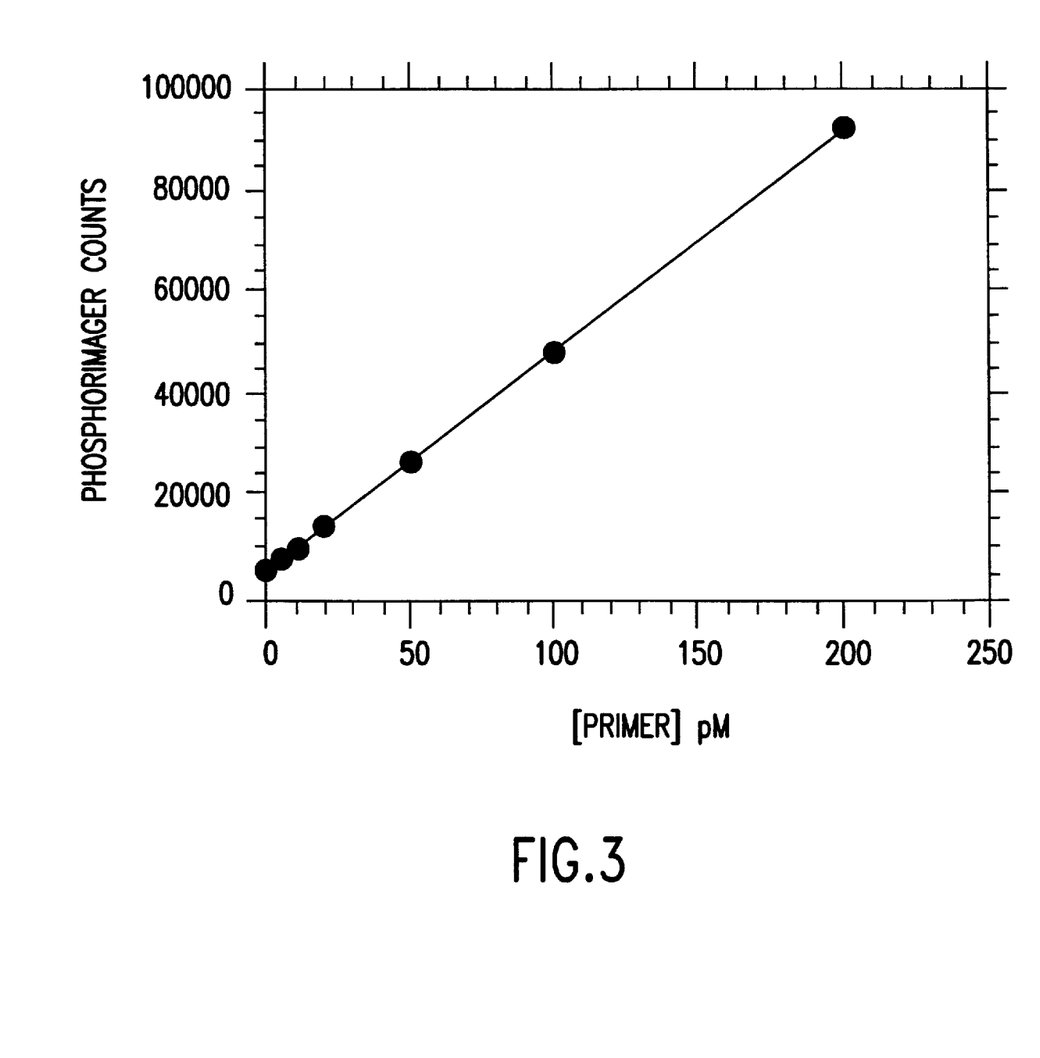
FIG. 3 is a graph demonstrating the linear response of DNA polymerase amplification. Reactions were carried out as described in Example 2. The line drawn through the points is a linear least-squares fit to the data with a correlation coefficient of 0.9999.

It has been found in accordance with this invention that the polymerase extension reaction can be conveniently monitored by filtration through nylon membranes. Under the conditions described, quantitative binding of the extended product can be observed, with only a small amount (less than 0.0003% ) of the unincorporated $\alpha^{32}$P-dGTP being retained on the nylon membrane. For high volume screening purposes, the filtration process can be performed using a 96-well manifold and the filter bound radioactivity can be quantitated with either a phosphorimager device or a microplate scintillation counter. FIG. 3 shows the sensitivity and linear response using nylon membrane filtration and phosphorimager detection for extension of the 13 nt AlMV RNA primer. Excellent linearity is observed up to 200 pM primer in a reaction volume of 20 μL. Note that under typical assay conditions approximately 10% of the substrate will be converted to hybrid polymerase extension reaction product, corresponding to 40 pM of product; this amount is well within the linearity range and detection limits of the assay.

A background primer-independent reaction is observed which is manifest as a faint band running above the major extension products across all lanes in FIG. 2 and as a nonzero y-intercept in FIG. 3. In the absence of template, the former background signal is absent and the latter is dramatically reduced, suggesting that they are correlated. The background signals are independent of the present of influenza core protein but they are dependent on Sequenase®. Thus, the background is due to a Sequenase®-catalyzed addition of $\alpha$-$^{32}$P dGTP to the single-stranded template. Much higher background signals are observed using a template in which the 3'-OH group is not blocked by an aminolinker moiety, suggesting that the reaction requires a free 3'-OH. The background signals can be further reduced by treatment of the aminolinker-blocked template with ddATP and terminal deoxy-nucleotidyl transferase, which suggests that presence of a free 3'-OH containing impurity in the template.

Figure 4:
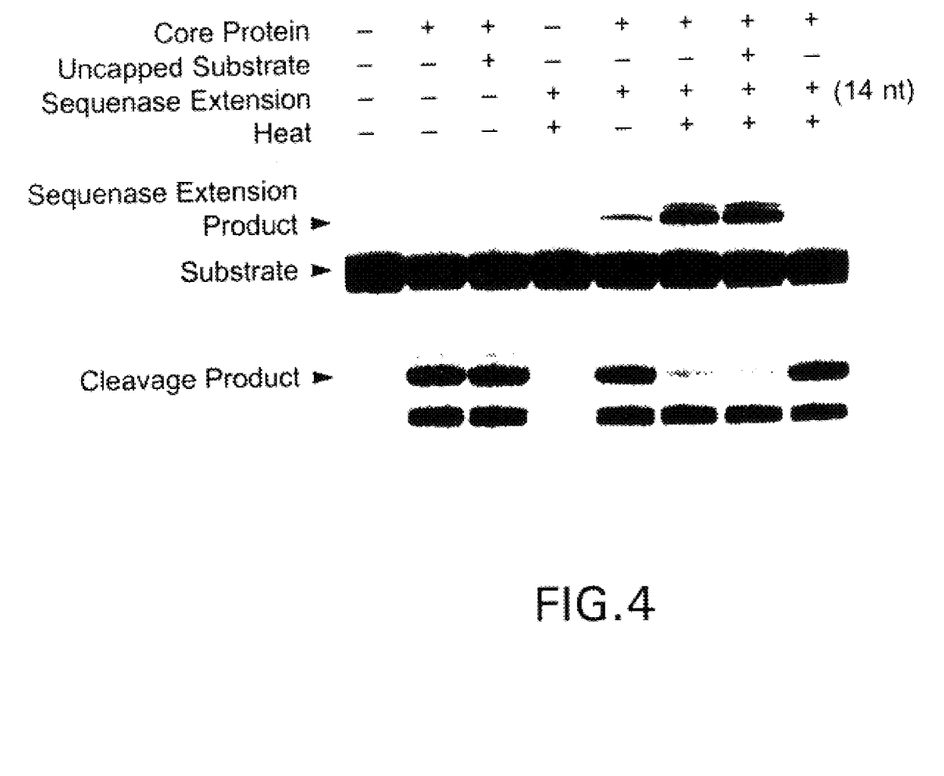
FIG. 4 is a gel demonstrating polymerase-catalyzed extension of the influenza endonuclease cleavage product, as described in Example 1.

In order to clearly characterize the coupled influenza endonuclease/polymerase extension process, a series of reactions were carried out using m$^7$G$^{32}$p- labeled AlMV substrate and unlabeled dGTP and were analyzed by gel electrophoresis. FIG. 4 shows that in the absence of core protein the AlMV substrate migrates as a single band corresponding to a length of 19 nt. Incubation of substrate with influenza core protein results in a major cleavage product as well as minor products that are shorter. The major product corresponds to cleavage at A13; this product is extended upon incubation with GTP. Similar results have previously been reported using the full-length AlMV RNA 4 (Plotch et al., 1989 *Cell* 23:847–858). The addition of a 10-fold excess of unlabeled, uncapped AlMV substrate does not affect the extend of cleavage. Incubation of substrate with Sequenase®, template and dGTP does not result in any extension in the absence of influenza core protein. Cleavage of substrate by core protein following by polymerase extension results in the appearance of a faint band above the substrate band. This band corresponds to the addition of 10 dG residues to the 13 nt product. Note that in this sample the bulk of the cleavage product is not extended by Sequenase®. In contrast, in the sample which is incubated at 80° C. for 1 minute following cleavage, near-quantitative extension is observed. The dissociation of the cleavage product is likely to be quite slow and the heating step may serve to release the bound product by denaturing the influenza endonuclease complex. A faint band observed above the polymerase extension product likely corresponds to addition of an extra dG residue to the blunt-ended extended primer:template duplex, as was observed in FIG. 2. As in the case of the cleavage reaction alone, the polymerase extension assay is not affected by the presence of a 10-fold excess of unlabeled, uncapped AlMV substrate. In the last lane, the 24 nt template that contains a 14 nt complementary region was added instead of the 13 nt complementary template. The specific cleavage product is not extended in this sample, which confirms that the major product corresponds to cleavage at A13 and not at A14.

The DNA polymerase extension assay was validated for detecting influenza endonuclease inhibitors by using the inhibitor, (4-[N-benzene-sulfonyl-3-(4-chlorobenzyl) piperidin-3-yl]-2,4-dioxobutanoic acid), which we have previously identified using the gel-based assay. This compound is similar to the 4-substituted 2,4-dioxobutanoic acids recently described as inhibitors of the influenza endonuclease (Tomassini et al., 1994 *AntiMicrob. Agents Chemother.* 38:2827–2837). Titrations of the inhibition of the endonuclease by this compound were performed using a gel based assay and the DNA polymerase extension assay of this invention under the same experimental conditions. The IC$_{50}$ values determined by fitting the data obtained over a range of 3 nM to 10 $\mu$M to a simple hyperbolic inhibition model are 260±60 nM for the gel assay and 220±50 nM for the DNA polymerase extension assay. Within error, the potency of this compound is the same in both assays, indicating that the DNA polymerase extension assay accurately monitors inhibition of the influenza endonuclease.

In another aspect of this invention, the DNA polymerase extension assay provides a convenient method to determine the cleavage position of capped substrates. In the past, the site of cleavage by an endonuclease was determined by generating sequence ladders with alkaline digestion or by digestion with RNases and electrophoresis. The former method suffers from ambiguities arising from lability of the m7G residue in the cap structure to alkaline hydrolysis and the latter from the faster electrophoretic mobility of the 3'-phosphorylated sequences generated by RNases relative to the unphosphorylated 3'-OH ends generated by the endonuclease. In contrast, the cleavage site can be unambiguously defined using the DNA polymerase extension assay of this invention by comparing the extension reactions catalyzed using templates with complementary regions corresponding to the expected cleavage products. FIG. 4 illustrates this aspect of the invention, where the template with a 13 nt complementary region serves as a substrate, whereas the 14 nt complementary template does not.

Another major advantage of the extension assay of this invention over existing methodologies is that the oligonucleotide product of interest can be detected in the presence of other nucleotides provided that they do not serve to prime polymerization. Thus, precise measurements of the reaction of interest can be performed even in complex, impure preparations. This is particularly helpful in monitoring ribozyme-mediated cleavage reactions.

The following non-limiting Examples are presented to better illustrate the invention.

EXAMPLES

General Experimental Methods: Oligo-deoxyribonucleotides and uncapped oligo-ribonucleotides were synthesized by Midland Certified Reagent Company (Midland, Tex.) and were purified by anion-exchange HPLC. Triphosphorylated oligonucleotides were synthesized and capped as described in co-pending patent application U.S. Ser. No. 08/480,068, filed Jun. 07, 1995, parent application of divisional application U.S. Ser. No. 08/807,104, filed Feb. 04, 1997, now U.S. Pat. No. 5,861,501 granted Jan. 19, 1999 (Attorney Docket No. 19406, filed herewith), which is hereby incorporated by reference. The sequence of the 19 nt substrate oligo-ribonucleotide is 5'-ppp-G(2'-OMe)UUUUUAUUUUUAAUUUUC-3' (SEQ.ID.NO.:1). 3'-Truncated ribonucleotides were also synthesized which correspond to the 5'-region of the substrate with lengths of 14, 13, 12, 10 and 6 nt. Unless otherwise indicated, a 23 nt template was used in all experiments with the sequence: 5'-Biotin-CCCCCCCCCCTAAAAATAAAAAC-amino-3' (SEQ.ID.NO.:4), where the 5'-biotin is N-biotinyl-6-aminohexyloxyphosphoryl moiety and the 3'-amino is 3-amino-2-hydroxy-propoxyphosphoryl. For some experiments a 24 nt template was used with the sequence: 5'-Biotin-CCCCCCCCCCTTAAAAATAAAAAC-amino-3' (SEQ.ID.NO.:5). $\alpha$-$^{32}$P-dGTP (3000 Ci/mmole) was obtained from Dupont NEN. Unlabeled dGTP was obtained from Pharmacia. Sequenase® Version 2.0 was obtained from United States Biochemicals (Cleveland, Ohio).

Unless otherwise noted, the polymerase extension reactions contained 1 nM primer, 50 nM template, 500 nM Sequenase®, and 500 nM dGTP and were carried out for 2 hours at the indicated temperature. The reactions were analyzed on 20% polyacrylamide 8M urea gels.

EXAMPLE 1

Cleavage Reactions and DNA Polymerase Reactions

Influenza cleavage reactions were performed at 25° C. in a buffer containing 100 mM tris[hydroxymethyl]aminomethane (Tris), pH 8.0, 50 mM KCl, 0.25 mM $MgCl_2$, 5 mM dithiothreitol (DTT), 4% (v/v) dimethyl sulfoxide (DMSO), in DEPC treated water. Polymerase extension reactions were performed in the same buffer, except that the $MgCl_2$ concentration was increased to 10 mM and the DMSO concentration to 9%. 500 nM dGTP was employed in extension reactions using end-labeled primers and a mixture of 50 nM $\alpha$-$^{32}$P-dGTP and 450 nM unlabeled dGTP was employed with unlabeled primers. Unless otherwise indicated, extension reactions were performed at 0° C. For the inhibition measurements, the compound 4-[N-benzenesulfonyl-3-(4-chlorobenzyl)piperidin-3-yl]-2,4-dioxo-butanoic acid was preincubated with influenza core protein for 10 min. The cleavage reactions were initiated by adding 0.4 nM of unlabeled (gel assay) or end-labeled (DNA polymerase extension assay) substrate in a 15 μL volume reaction containing 0.75 μL influenza core protein and were run for 10 min at 25° C. For the DNA polymerase extension assay, the extension reaction was carried out in a 20 μL volume containing 50 nM Sequenase®, 500 nM dGTP, 50 nM template of 18 h at 0° C.

Reactions were analyzed either by electrophoresis in 20% polyacrylamide gels containing 8M urea or by filtering through 0.2 μm pore Nytran® membranes in a 96-well manifold (Schleicher and Schuell, Keene, N.H.). For filtration, samples were diluted with 200 μL of 250 mM EDTA, pH 8.0 and 200 μL was loaded onto the membrane equilibrated in 5X SSC (0.75M NaCl, 75 mM sodium citrate, pH 7.0) and filtered immediately. Each well was washed five times with 200 μL of 5SSC, and the filter was removed from the manifold washed 3 times in 100 ml of 5X SSC.

Gels were visualized and filters were quantitated using a Phosphorimager® (Molecular Dynamics, Sunnyvale, Calif.) with the Imagequant® software provided by the manufacturer. In some experiments, the Nytran® filters were also quantitated using a TopCount® (Packard Instruments, Meriden, Conn.) microplate scintillation counter using Flexifilter® kits and Microscint® O scintillation fluid.

EXAMPLE 2

DNA Polymerase Extension Assay For Ribozyme Cleavage.

Kinetic reactions are performed according to the procedure of Fedor and Uhlenbeck 1990, Proc. Natl. Acad. Sci USA 87:1668–1672, which is hereby incorporated by reference, using ribozyme concentrations of 1 nM, 10 mM divalent metal ion and RNA substrate concentrations of 50 nM. The DNA polymerase extension reaction is carried out sing 50 nM Sequenase®, 500 nM labeled dATP, 100 nM capture oligonucleotide/template for 18 hours at 0° C. Reactions are analyzed by the methods described above.

---

What is claimed is:

1. A method of detecting site-specific ribozyme activity in a sample comprising:
   a) adding a ribozyme substrate to a sample comprising a ribozyme and a putative ribozyme inhibitor whose activity is to be assayed, to generate an RNA product;
   b) hybridizing RNA product with a DNA template, said DNA template comprising a first 3'-segment substantially complementary to the RNA product and a 5'-extension region, said 5'-extension region comprising at least 10 substantially repeated nucleotides, under hybridization conditions to form a RNA:DNA heteroduplex structure;
   c) adding radiolabeled mononucleotide which is complementary to the substantially repeated nucleotides;
   d) adding DNA polymerase to the heteroduplex structure under conditions permitting the DNA polymerase to catalyze the addition of the labeled nucleotide to the 3'-end of the RNA product, to produce a radiolabeled polymerase product; and
   e) filtering the sample with a containing the radiolabeled polymerase product and excess radiolabeled mononucleotide by passing the sample through a nylon filter so that the radiolabeleed polymerase product is trapped by the filter; and
   f) measuring the amount of radiolabeled polymerase product trapped on the filter and comparing that amount to that obtained when no ribozyme inhibitor is present in a control sample as a measure of the site-specific ribozyme activity in the sample.

2. A method of determining the site where a site-specific nuclease cleaves an oligonucleotide substrate to create a cleavage product comprising:
   a) preparing at least one DNA template oligonucleotide, wherein the DNA comprises a first 3' region thought to be complementary to the cleavage product and thought to be of the same length as the cleavage product, ad a 5'-extension region, comprising at least one nucleotide;

b) adding cleavage product to the sample under hybridizing conditions to form a RNA:DNA heteroduplex or DNA:DNA duplex structure;

c) adding to the sample labeled mononucleotide which is complementary to the 5'-extension region;

d) adding to the sample DNA polymerase under conditions permitting a polymerase reaction to occur wherein the labeled mononucleotide is added to the 3'-end of the cleavage product if the 5'-segment of the DNA template is complementary to the cleavage product and of the same length as the cleavage product; and e) determining whether a nucleotide is added to the cleavage product as a measure of the amount of site-specific nuclease activity in the sample.

3. A method according to claim 2 wherein a plurality of DNA oligonucleotide templates are prepared in step 1, each having a first 3' region differing in length.

4. A method of detecting a site-specific ribozyme activity in a sample, wherein in the presence of a divalent cation, said ribozyme acts on an oligonucleotide substrate to generate a single-stranded oligonucleotide product comprising:

a) adding an oligonucleotide substrate to the sample to be assayed to generate an oligonucleotide product;

b) hybridizing the oligonucleotide product with a DNA template, said DNA template comprising a first segment substantially complementary to the oligonucleotide product and a template 5'-extension region, said 5'-extension region comprising a single or substantially repeated nucleotide, under hybridization conditions to form a RNA:DNA heteroduplex or a DNA:DNA duplex structure;

c) adding labeled mononucleotide which is complementary to the 5'-extension region of the DNA template;

d) adding a DNA polymerase to the heteroduplex or duplex structure under conditions permitting the DNA polymerase to catalyze the addition of the labeled mononucleotide to the 3'-end of the oligonucleotide product to produce a labeled polymerase product; and e) measuring the amount of labeled polymerase product as a measure of the amount of site-specific ribozyme enzyme activity in the sample.

5. The method according to claim 4 wherein the sample to be assayed contains a putative inhibitor of ribozyme activity.

6. The method according to claim 5, further comprising comparing the amount of ribozyme activity of the sample to the activity determined for a control sample comprising the same ribozyme which is not in the presence of a putative inhibitor.

* * * * *